US010140504B2

(12) United States Patent
Finkelstein et al.

(10) Patent No.: US 10,140,504 B2
(45) Date of Patent: Nov. 27, 2018

(54) SYSTEM AND METHOD UTILIZING FACIAL RECOGNITION WITH ONLINE (SOCIAL) NETWORK TO ACCESS CASUALTY HEALTH INFORMATION IN AN EMERGENCY SITUATION (71) Applicants: David Alan Finkelstein, Boca Raton, FL (US); Paige Erin Finkelstein, Boca Raton, FL (US)

(72) Inventors: David Alan Finkelstein, Boca Raton, FL (US); Paige Erin Finkelstein, Boca Raton, FL (US)

( * ) Notice: Subject to any disclaimer, the term of this patent is extended or adjusted under 35 U.S.C. 154(b) by 25 days.

(21) Appl. No.: 15/293,886

(22) Filed: Oct. 14, 2016

(65) Prior Publication Data
US 2017/0109570 A1  Apr. 20, 2017

Related U.S. Application Data (60) Provisional application No. 62/241,232, filed on Oct. 14, 2015.

(51) Int. Cl.
| G06K 9/00 | (2006.01) |
| G06F 19/00 | (2018.01) |
| G06F 21/62 | (2013.01) |
| G06Q 50/00 | (2012.01) |
| H04L 29/08 | (2006.01) |
| G16H 10/60 | (2018.01) |
| H04L 29/06 | (2006.01) |
| H04W 12/06 | (2009.01) |
| H04W 4/90 | (2018.01) |

(52) U.S. Cl.
CPC ......... *G06K 9/00288* (2013.01); *G06F 19/00* (2013.01); *G06F 19/321* (2013.01); *G06F 21/6245* (2013.01); *G06Q 50/01* (2013.01); *G16H 10/60* (2018.01); *H04L 67/10* (2013.01); *H04L 67/306* (2013.01); *H04L 63/0861* (2013.01); *H04W 4/90* (2018.02); *H04W 12/06* (2013.01)

(58) Field of Classification Search
CPC .............. G06K 9/00288; H04L 67/306; G06F 21/6245; G06Q 50/01
See application file for complete search history.

(56) References Cited

U.S. PATENT DOCUMENTS

| 9,330,235 | B2 | 5/2016 | Walton, III | |
| 2008/0166992 | A1* | 7/2008 | Ricordi | A61B 5/0002 455/404.2 |
| 2009/0136094 | A1 | 5/2009 | Driver et al. | |
| 2012/0124202 | A1* | 5/2012 | Cooper | G06F 17/30035 709/224 |
| 2015/0087257 | A1* | 3/2015 | Balram | H04W 4/12 455/404.1 |

* cited by examiner

*Primary Examiner* — Qian Yang
(74) *Attorney, Agent, or Firm* — Dunlap Bennett & Ludwig PLLC; Brendan E. Squire (57) ABSTRACT A system and method for a participant to securely store select preexisting medical and other information which is then available in real time to emergency workers using a (mobile) software application that uses facial recognition to match a presenting image of a casualty with a master image of the participant to provide their identity. Once identified, pre-existing medical and demographic information may be transmitted to emergency responders to better care for the casualty in an emergency situation.

19 Claims, 8 Drawing Sheets

ERINFO — 10

SAMPLE PRIVATE PROFILE CONTENT

*BY DEFAULT, USERS ARE NOT OBLIGATED TO ENTER ANY INFORMATION; HOWEVER, PATIENTS WITH PRE-EXISTING CONDITIONS WOULD BENEFIT MOST BY PROVIDING INFORMATION.

- ADDRESS
- EMERGENCY CONTACT INFORMATION
- DATE OF BIRTH
- WEIGHT
- BLOOD TYPE/DISORDERS
- ALLERGIES
- MEDICAL DISORDERS
- MEDICATIONS
- NATIVE LANGUAGE
- TWIN
- ORGAN DONOR ELECTION
- IMAGES OF OTHER UNIQUE IDENTIFIERS (EG TATTOOS)
- OTHER

PRIVACY: AT ALL TIMES, SERVICE PROVIDER (AND ITS PARTNERS) WILL DO THE UTMOST TO ENSURE CONSUMER CONFIDENTIALITY. APPLICATION IS NOT REQUIRED TO BE HIPPA COMPLIANT. ALL PATIENT INFORMATION IF OPT IN AND PROVIDED SOLELY AT THE DISCRETION OF THE PATIENT.

SYSTEM AND METHOD UTILIZING FACIAL RECOGNITION WITH ONLINE (SOCIAL) NETWORK TO ACCESS CASUALTY HEALTH INFORMATION IN AN EMERGENCY SITUATION

CROSS-REFERENCE TO RELATED APPLICATION

This application claims the benefit of priority of U.S. provisional application No. 62/241,232, filed Oct. 14, 2015, the contents of which are herein incorporated by reference.

BACKGROUND OF THE INVENTION

The present invention relates to facial recognition and on-line technologies, and more particularly to applying facial recognition to obtain a casualty identity. Incapacitated, confused or casualties otherwise unable to provide medical information are at risk of greater harm or death because emergency medical providers may be unaware of pre-existing medical conditions. Some medical conditions that place these individual at risk include: Diabetics, Epileptics, those with HIV+, Hepatitis or heart conditions, or have antibiotic, animal or other allergies.

In the United States alone there are over 136.5M Emergency room visits per year. Of that number, there are approximately 1 million unconscious or otherwise non-communicative patient ER arrivals per year, with about 650 thousand John or Mary Doe ER admissions. Research studies indicate that there is a better survival rate for those patients whose identity eventually becomes known. Conventionally, medic alert bracelets have also improved medical outcomes and facilitated patient identification.

Emergency Medical Technicians (EMTs), Paramedics and Emergency Room personnel need quick access to a casualty's pre-existing medical conditions and other vital medical information when the casualty is incapacitated or otherwise (i.e. language, age or dementia) unable to provide it.

Previous systems for utilizing facial recognition technology to obtain or confirm a patient identity, such as that disclosed in U.S. Patent Application No. 2009/0136094 require that the patient be known to the system. That is, in a health care setting or patient administration system, the patient has previously registered with the system. The health care facility or plan, as part of the registration process, would capture an image of the patient and maintain it as part of the patient's records. In these circumstances, the subsequent use of facial recognition technologies to identify the patient within the system, is in a sense, just an extension of barcode, and similar technologies, for confirming the identity of a patient during a subsequent patient contact.

These systems find good application within a healthcare facility or a healthcare network utilizing a proprietary network, hardware, and software and requires ongoing operating costs be borne by the providing institution. These systems are proprietary and are not generally available to users beyond the confines of the institution in which they reside. These systems are of limited to no value in emergency settings, typically remote from a healthcare facility, where the identity of a casualty is unknown.

As can be seen, there is a need for a generalized and globally accessible system and method for improving the identification of a casualty at an injury or incident site, or on presenting at an Emergency services health care facility on an initial encounter with that facility.

SUMMARY OF THE INVENTION

One aspect of the present invention includes a method of automatically identifying a casualty. The method includes receiving a presenting image of the casualty at a server hosted by a casualty identification service. The server is in communication with a database containing a master image and an identity profile corresponding to a member of the casualty identification service. The method includes running a facial recognition engine to compare the presenting image to the master image and determining a matching identity of the casualty. If a matching identity is found, transmitting the identity profile of the member to a medical provider in an emergency medical services system.

In certain embodiments, the identity profile includes one or more health conditions pertaining to the member. In other embodiments, the identity profile includes In Case of Emergency (ICE) contact information of the member. In yet other embodiments, the identity profile includes one or more allergy conditions pertaining to the member.

The method may also include receiving the presenting image from a first responder. The method may verify the medical credentials of the first responder. The method may also monitor access to the casualty identification system by the first responder.

In other aspects of the invention, if a matching identity is not found, the method may include running a social network interface to obtain the matching identity from a participating social media network. The master image and the identity profile corresponding to the member may be received via an application program interface (API) provided to the participating social media network.

Embodiments of the invention may verify the ICE contacts and may also provide a notification to one or more of the ICE contacts if the member is identified as the casualty.

In yet other aspects of the invention, a system for automatically identifying a casualty, is disclosed and claimed. The system includes comprising: a server hosted by a casualty identification service. The server is in communication with a database containing a master image and an identity profile corresponding to a member of the casualty identification service. An emergency provider authentication module is configured receive a presenting image of the casualty from a mobile computing device operated by an authenticated emergency provider. A facial recognition engine configured to compare the presenting image to the master image to determine a matching member identity of the casualty.

The emergency provider authentication module may be configured to transmit the identity profile corresponding to the matching member identity. The system may also include an In Case of Emergency (ICE) noitifier engine that is configured to notify one or more emergency contacts of the matching member.

In certain embodiments of the system, an application program interface (API) communicates with a participating social media network, and is configured to link the member to the casualty information service via the participating social media network. In some instances, the system is configured so that the presenting image is compared to an identified image of the member on the social media network.

Other aspects of the invention include a computer program product stored on a non-transitory computer storage medium with machine-readable program code for causing, when executed, a computer to perform process steps. The steps include receiving a presenting image of a casualty at a server hosted by a casualty identification service, running a facial recognition engine to compare the presenting image to a master image associated with an identity profile of a member of the casualty identification service; and determining a matching identity of the casualty. If a matching identity is found the steps include transmitting the identity profile of the member to a medical provider in an emergency medical services system.

The identity profile may include one or more of: a health condition pertaining to the member; an In Case of Emergency (ICE) contact information pertaining to the member; an allergy conditions pertaining to the member; and a medicine taken by the member. The process steps may also include receiving the presenting image from a first responder. In other embodiments, the process steps include, accessing a member profile on a participating social media network. In addition, the process steps may include performing the facial recognition on the participating social media network.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a system and method for responding EMTs, Paramedics, or Emergency Room personnel to utilize facial recognition to provide an identification of a medical casualty by matching a presenting image of the casualty with one or more images from the casualty's social media profile(s) or other facial images known to the system. The system of the present invention is globally accessible to individuals before an emergent health care condition arises and does not require an individual's affiliation or association with a healthcare provider, a network of healthcare providers, a healthcare system, or health insurance provider. Similarly, the system of the present invention is globally accessible to all EMS first responders and is capable of providing vital identification and medical information to the EMS personnel, regardless of the casualty's affiliation with any healthcare provider, healthcare network, system, or insurance provider. In preferred embodiments, the system of the present invention is a cloud based system that is readily extensible in the event of a localized mass casualty event or a series of widely dispersed concurrent casualty events.

As used herein, a presenting image is an image of a casualty that is taken by a medical first responder at the scene of a medical emergency, upon a casualty presenting to an emergency room of a medical treatment facility, or other presenting encounters of a casualty in need of receiving emergency medical treatment. A casualty is a person who has been injured or is otherwise is in need of healthcare services that has not been admitted to a healthcare facility.

An embodiment of a system 10 according to aspects of the present invention may be referred to as ERinfo.me, which is a consumer technology platform where an individual, parent, or guardian can securely store select pre-existing medical and other vital information, for themselves, or for their children, or those in their care. Upon enrollment, the registered information is then available in real time to emergency workers, for example via a (mobile) software application that employs facial recognition to match a presenting image of the casualty with their registered information should they be incapacitated or otherwise non-communicative during an emergency.

Figure 1:
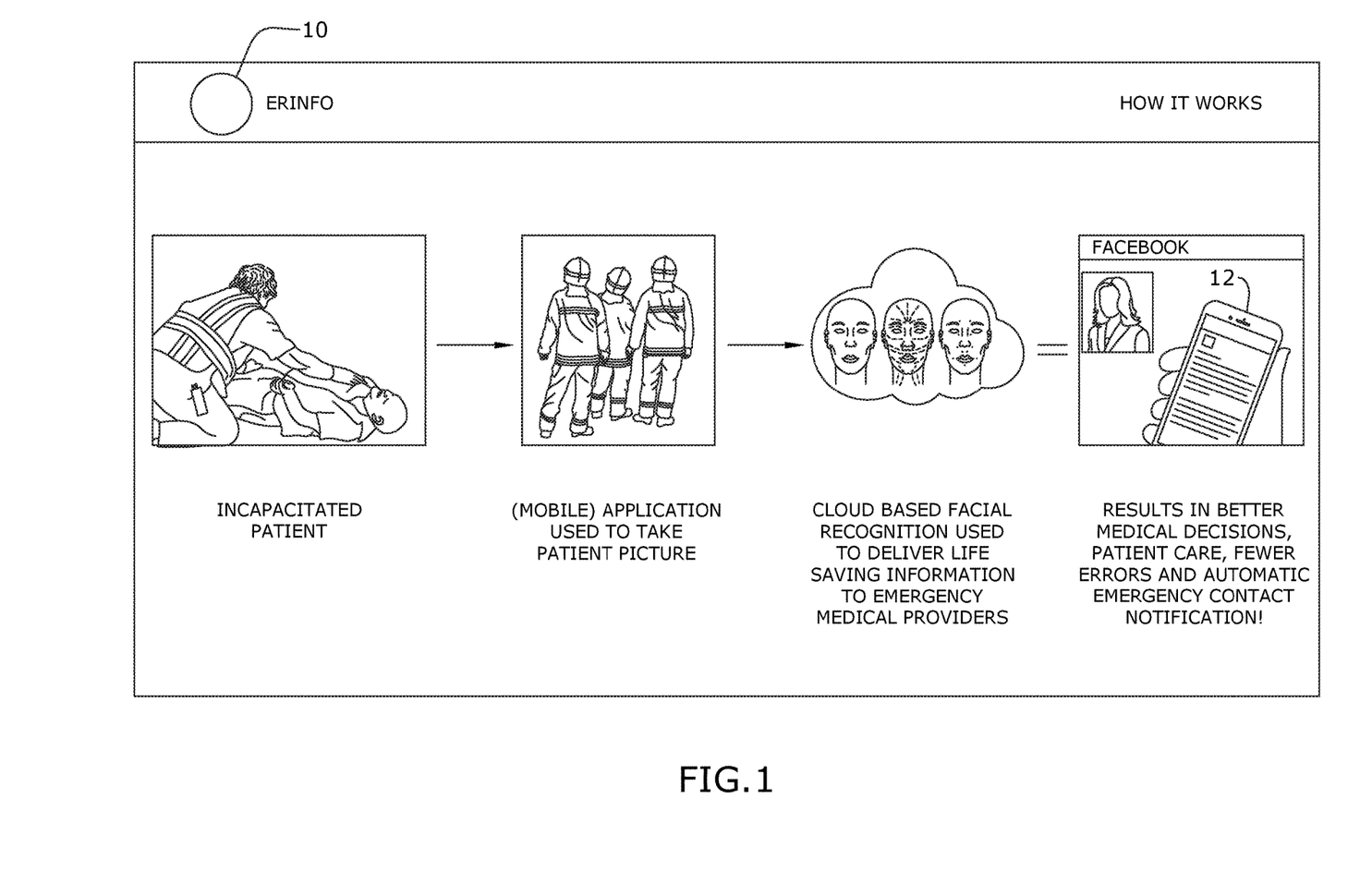
FIG. 1 is a graphical depiction of an embodiment of the system illustrating its use.

As seen in reference to FIG. 1, the presenting image may be obtained, for example, by a first responder utilizing a mobile computing device 12, such as a mobile phone, a tablet, or other network connected imaging device. In an initial presenting encounter, shown at block A, a first responder or other medical care provider encounters an incapacitated casualty or a casualty that is otherwise unable to communicate with the first responder. At block B, the first responder utilizes a mobile computing device 12, to take a picture of the casualty's face. At block C, the picture is transmitted by the mobile computing device, where a server or cloud based facial recognition is performed, which may include searching across one or more participating social media sites, such as Facebook, or a business network, such as LinkedIn, (collectively referred to herein as a social network) to identify the casualty.

If the casualty has registered with ERinfo or if the casualty has enabled their social media account to "opt-in" to become a participating end user of the system, the casualty is identified and at block D, the first responder is provided the casualty's identity and any medical conditions that the end user has elected to share as part of their participation in the ERinfo system 10.

Figure 2:
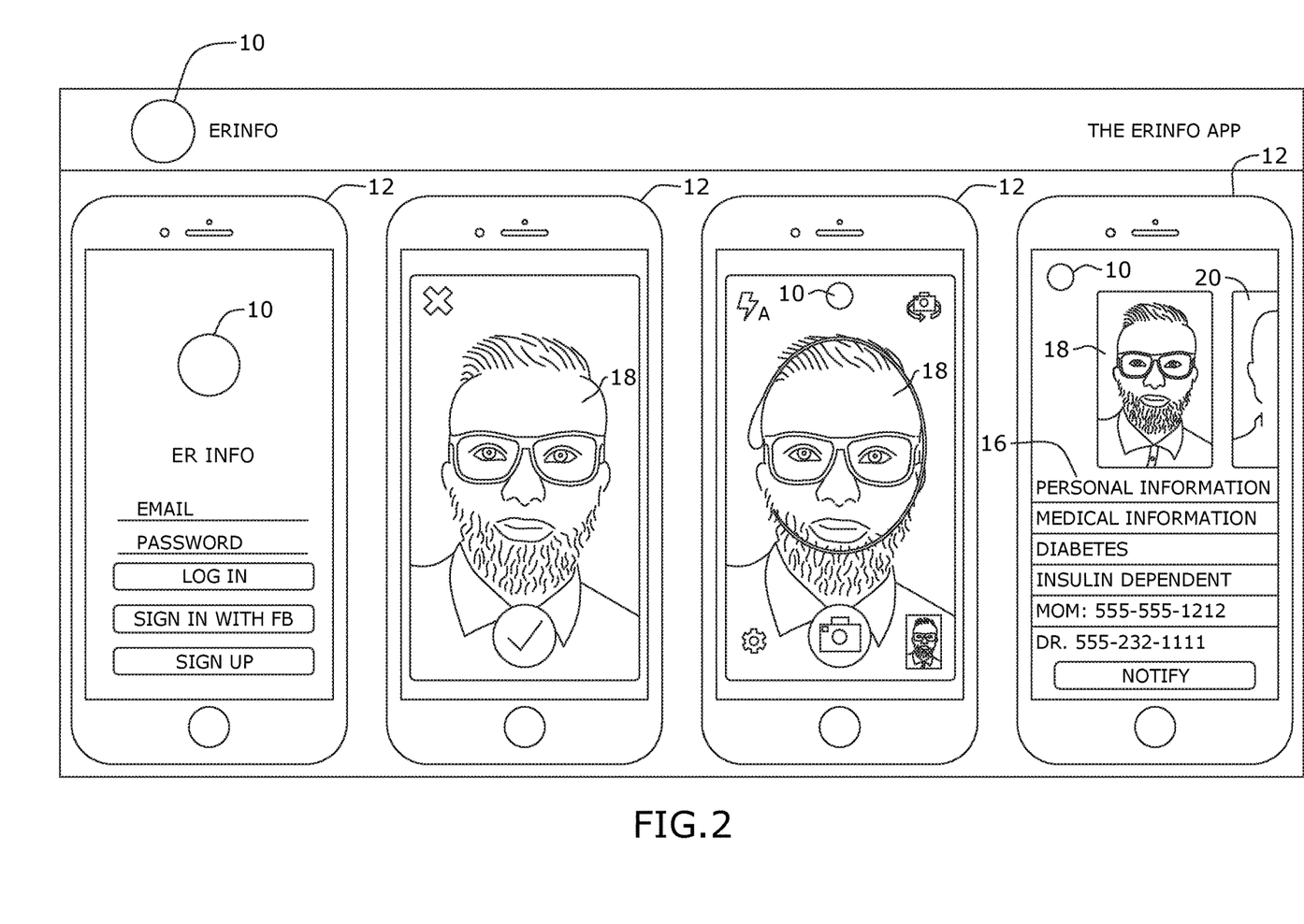
FIG. 2 is a series of user interface screens depicting an embodiment of a participant enrollment application.
Figure 3:
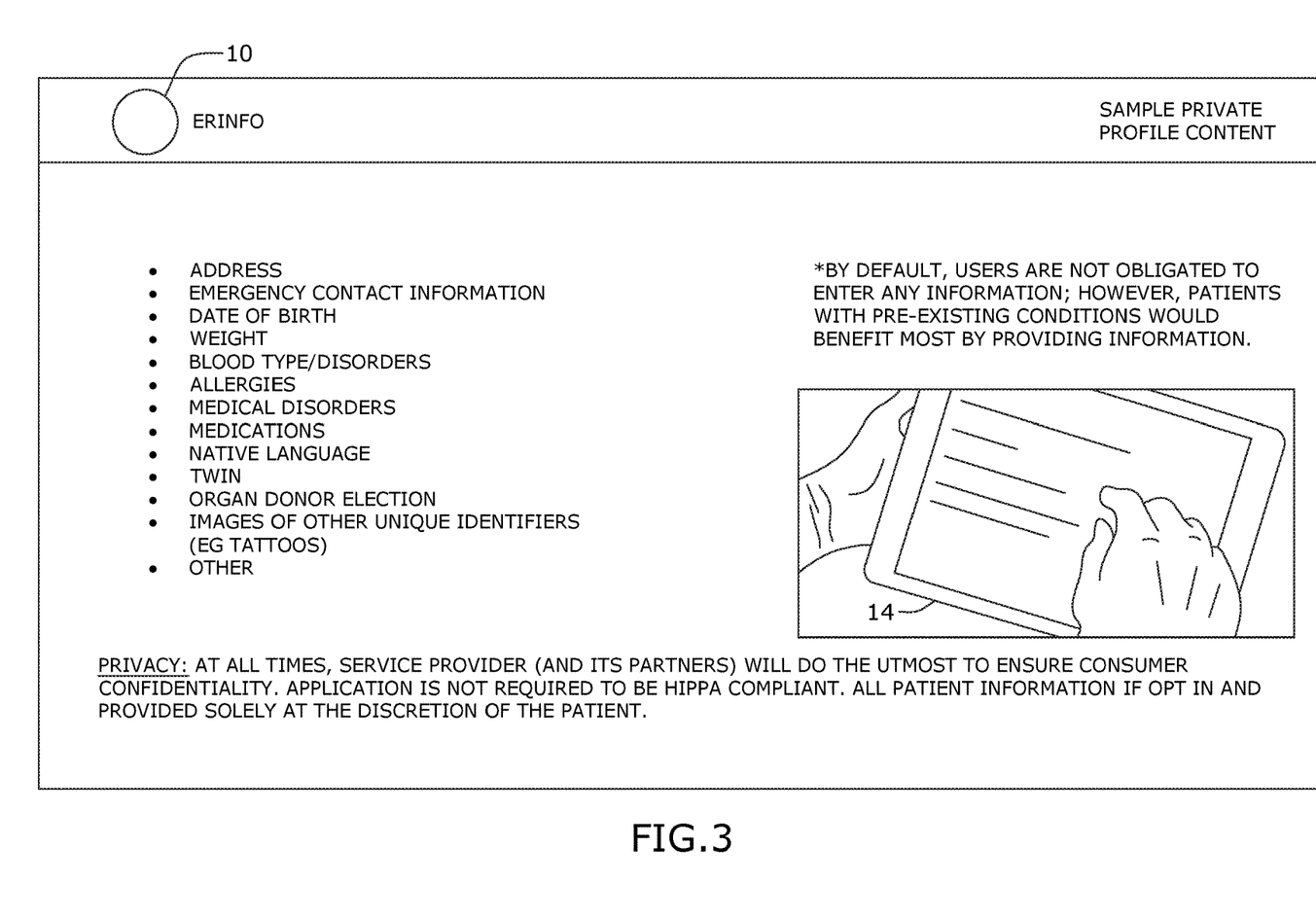
FIG. 3 is a table of private profile content for storage on a participant registration database.

As shown in reference to FIGS. 2 and 3, participants may pre-register pre-existing medical conditions that may be significant for receiving emergency medical treatment in the event that the participant becomes a casualty or is otherwise incapacitated. As seen in reference to FIG. 4, the participants may pre-register at block 20 and enroll their conditions via a web-based 21 or mobile application 22 linked to the ERInfo 10 according to the present invention. Pre-registration may also be provided via an independent third party partner web-site 23 or application linked to the present system 10. Third party partners include organizations such as the American Epilepsy Foundation, American Heart Association, American Diabetes Foundation, National Hemophilia Foundation, Aids Healthcare Foundation, Asthma and Allergy foundation, Alzheimer's Foundation of America, Dementia Foundation, Food Allergy Research and Education, participating medical health insurance plans, participating hospital and healthcare systems. Alternatively, participants may enroll via, a customized application program interface (API) link 24 provided through their social network provider(s), such as Facebook, Google+, LinkedIn, etc.

As stated above, EMTs, Paramedics and Emergency Room personnel need quick access to a participant's pre-existing medical conditions and other vital medical information when the participant is incapacitated or otherwise (i.e. age, language or dementia) unable to provide it. Participants may go online to a social network (i.e. Facebook) or the ERInfo servers, and securely and privately provide information about themselves and their pre-existing medical conditions. In like manner, information confirming the absence of a pre-existing medical condition for the person would also be important in an emergency situation.

If subsequently the participant is involved in an emergency situation where they are incapacitated, or otherwise cannot communicate, an emergency medical provider can use the ERinfo.me mobile app or web based app to access the participants' information from the social network or system servers. The emergency medical provider using their mobile phone, tablet or camera equipped computer takes a picture of the participant's face and uploads it to the social network or system server. Using the social media network's facial recognition capabilities or the invention's servers, the system's facial recognition engine matches the casualty's facial image with the participant's information and delivers it to the emergency medical provider.

In certain preferred embodiments, the system may be configured to obtain at least an identity of a casualty that has not pre-registered by accessing images retained in a social network. In other embodiments, the invention may also provide interfaces or a gateway to the participants Electronic Health Record.

The participant invention can be an anonymous database of participant pre-existing healthcare conditions (useful to drug companies, disease advocacy groups and disease specialists).

Health Condition Enrollment System

As indicated previously, the participant registration system can either be performed through the ERInfo.me system 10 via a web site 21, mobile app 22 or it may leverage an extension 23, 24 created and run using an existing profile residing on a third party partner or third party social networking application platform, such as Facebook, Google+ or LinkedIn, or other such network.

Figure 8:
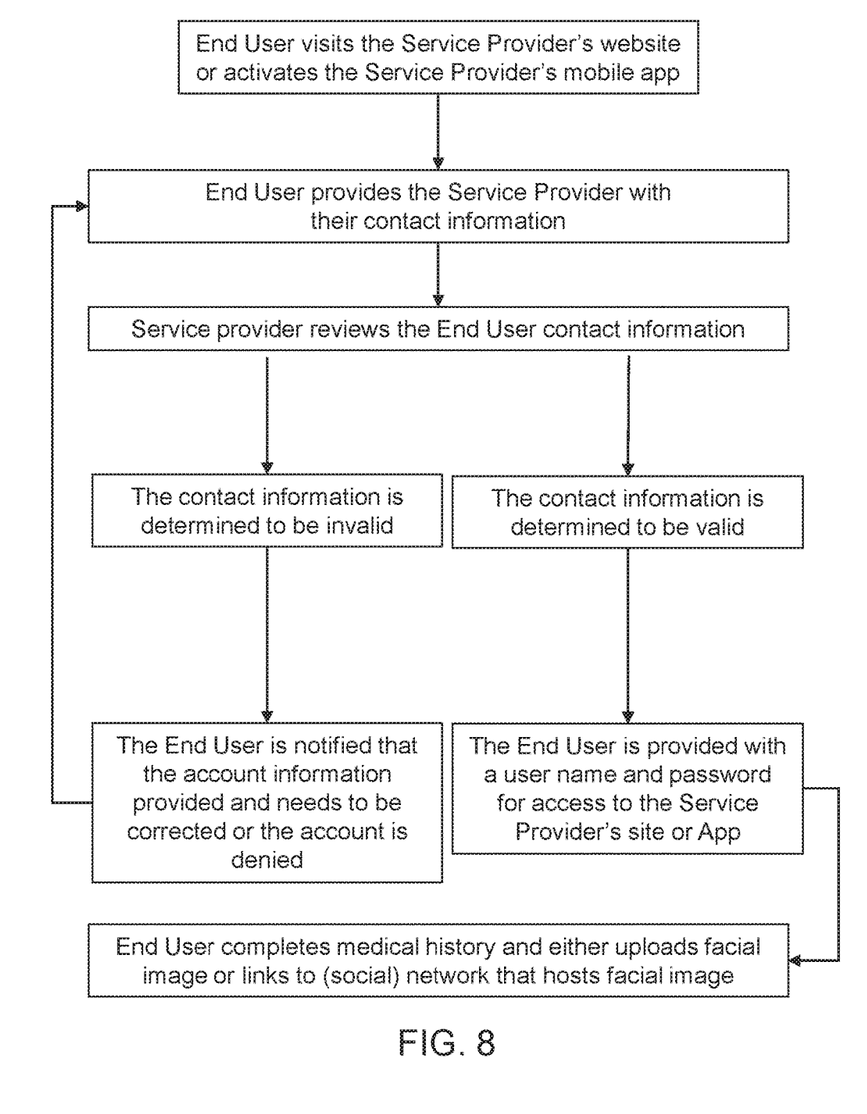
FIG. 8 is a representative flow chart for an end user signup for establishing an account.

As seen in reference to FIGS. 2 and 3, the registration process provides a participant with an easy interface in which to record and store the emergency health and contact information they may want to provide. By way of example, a mobile device 12 initial registration application user interface (UI) 22 is shown in FIG. 2. At 22A, the UI 22 prompts the user to establish an account with the system 10. A flow chart for a user account establishment and verification routine is depicted in reference to FIG. 8.

Figure 7:
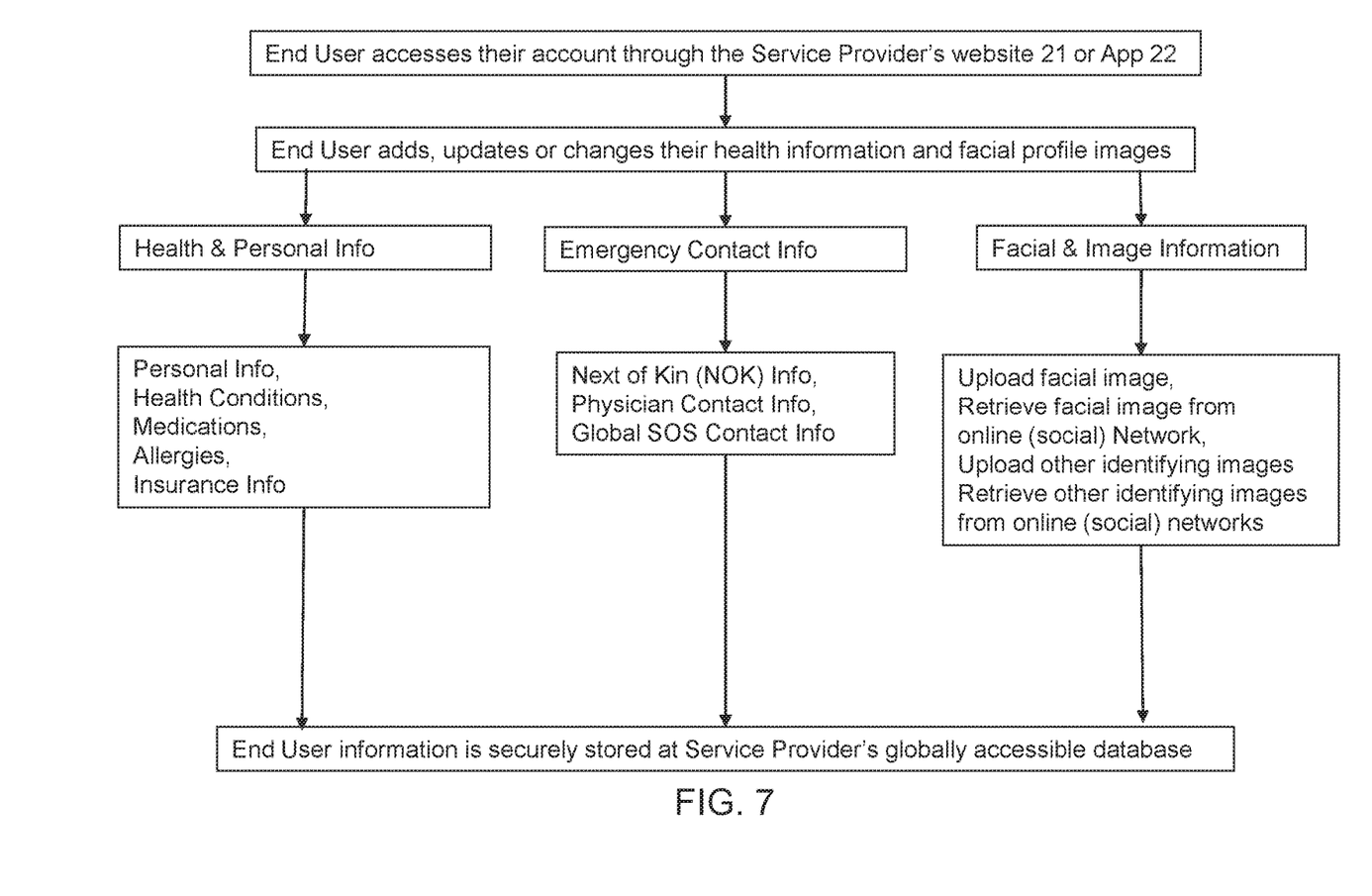
FIG. 7 is a representative flow chart for an end user information management process.

The UI 22 may then prompt the user to load one or more master images of the user. In the UI shown at 22B, the user may select an image stored on their mobile device 12. At 22C, the UI may be configured to prompt the user to take and store an image or images of themselves. The master images can be a "selfie" or the user may be prompted for a pre-existing online social media network profile picture or any other photo containing a face/head picture for facial recognition matching purposes. The master image, as well as the presenting image, may also track other images in the patient profile that include other identifying marks such as Tattoos, scars, or other distinguishing biometric attributes. Additional information that may be input by the user is illustrated in reference to FIGS. 3 and 7.

As seen in the UI shown at 22D, the registration process may also allow the user to include personal information 16, such as emergency points of contact, including a family members, a loved one, a personal physician, or other personal representative to notify in the event the participant is incapacitated. When a participant registers with ERInfo 10, an "In Case of Emergency or Next of Kin" (ICE/NOK) notifier engine 61 may be configured to send a message 62, such as a telephone call, an email and/or a SMS text message, to the participant's ICE/NOK contacts. The message 62 may include a confirmation link that directs the contact to confirm their info by either responding to the text or clicking on a link in the message 62. In the message 62 the ICE/NOK contact receives, and on the webpage for confirmations, there can also be a registration link for the ICE/NOK contact to register for ERInfo as well, thereby expanding awareness of the system and participation.

In embodiments of the system, the emergency contact may receive an automatically generated telephone call, email and/or SMS text message confirming the participant's enrollment. In other alternative embodiments, the enrollment system may also permit participants to load and store health insurance policy information.

Emergency Provider Application

Figure 4:
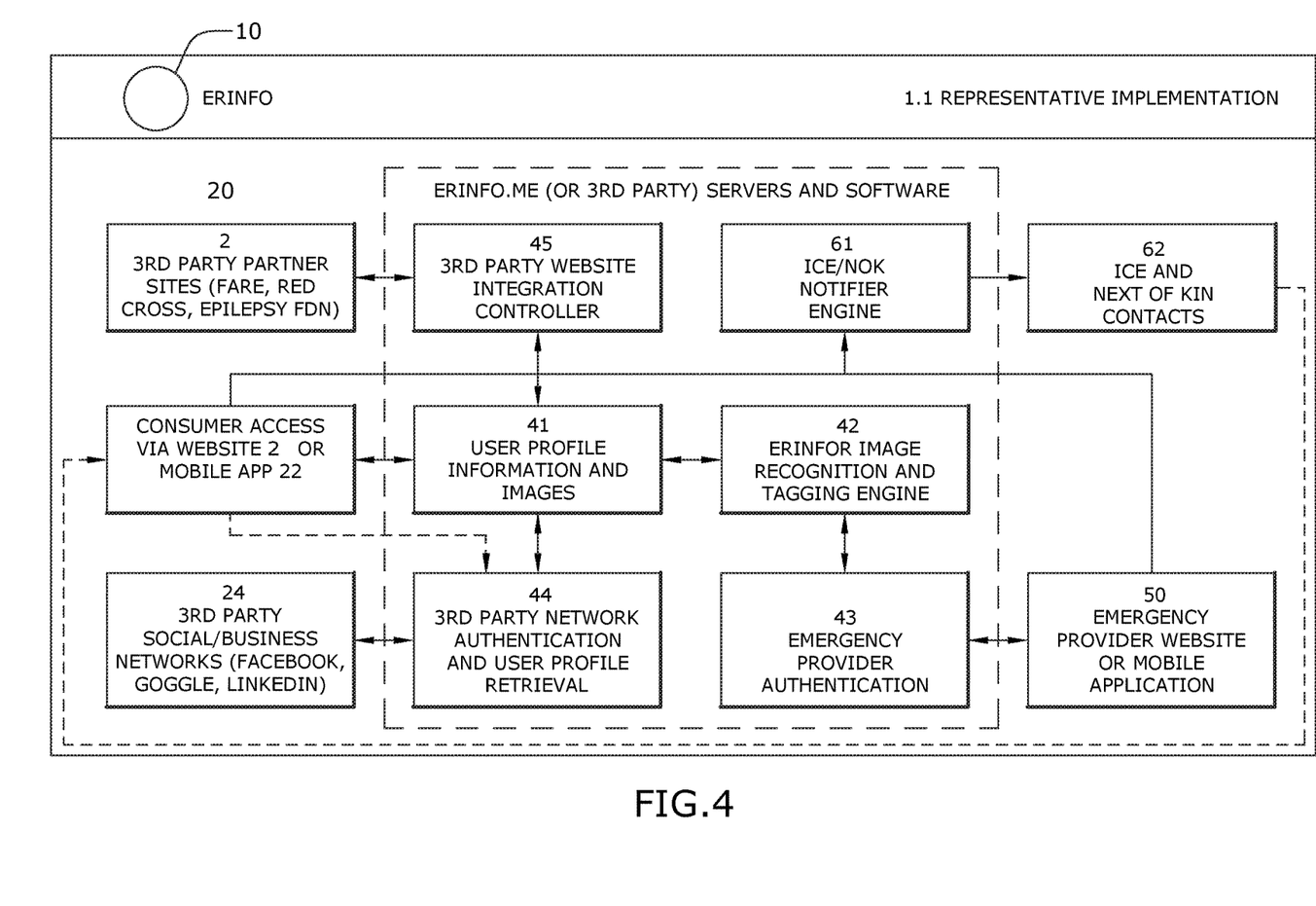
FIG. 4 is a representative system architecture for an embodiment of the present invention.

The system 10 of the present invention also includes an emergency provider application 50, which may be run either on the emergency healthcare provider's mobile computing device 12, such as a smart phone, tablet, or wearable computing technologies. Alternatively, the emergency provider application 50 may be accessed through a web interface from a laptop, desktop, or other computer. Access to the provider application 50 may be provided via an ERinfo.me provider only website. Alternatively, the provider application 50 may be enabled via high performance and lightweight proprietary mobile applications that run on mobile computing platforms 12 with minimal requirements such as, iOS (Apple) or Android operating system, a camera, and mobile data, wired or Wi-Fi internet connectivity. The provider app 50 may run in the background on an emergency provider's device 12. When needed, the provider app 50 opens displaying the device's camera interface.

Figure 5:
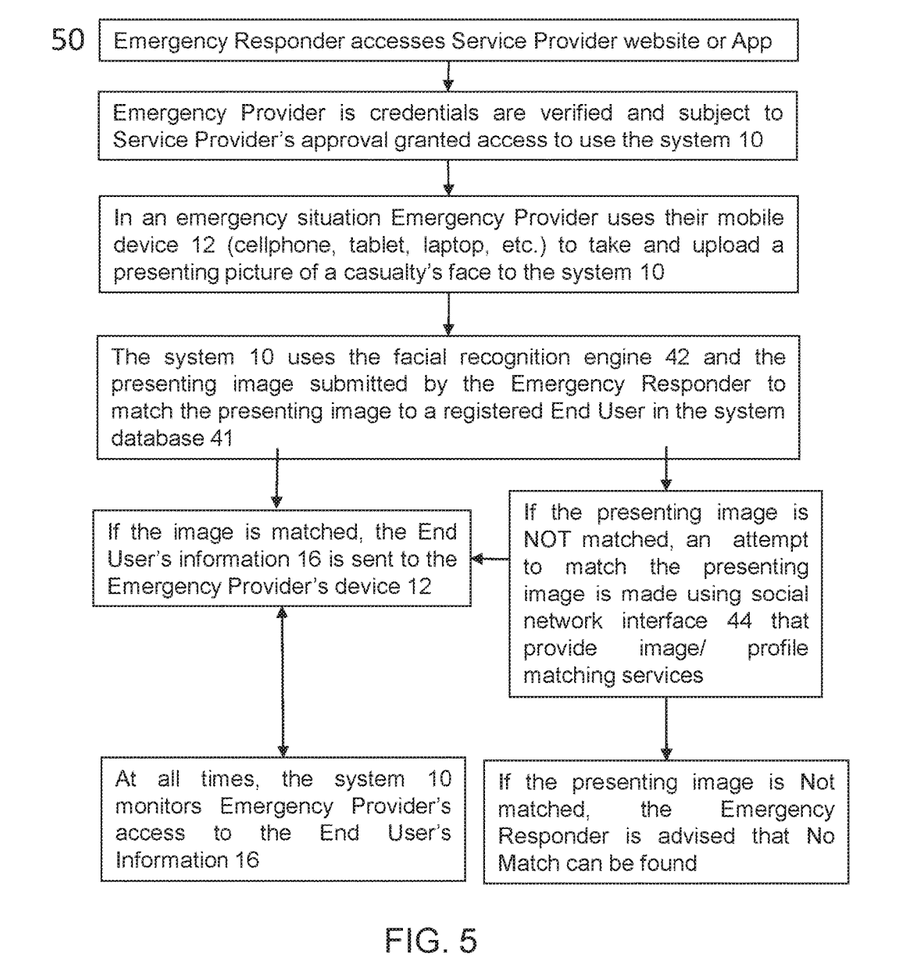
FIG. 5 is a representative flow chart for an Emergency Responder Application Use.

As seen in reference to FIG. 5, the emergency provider application 50 allows the healthcare provider to take a presenting picture of the incapacitated patient's face, and the application automatically prepares the picture and uploads the presenting picture to ERInfo 10 for recognition via the facial recognition engine 42. If a match is made on the server 10, then the application 50 receives identification information 16 and registered health conditions about the casualty, along with profile images and emergency contact information, when provided.

If a match is not made within the system database 41, the social network interface 44 is activated in an attempt to match the presenting image to a profile image within a participating social network. If a match is then made, the information matching the casualty 16 is provided to the emergency provider application 50. If no match is found on the participating social media networks, the emergency responder is notified that no match can be found.

During an emergency, and upon recognition, the Provider app may also offer the emergency provider a means to either automatically or semi-automatically contact the casualty's designated ICE/NOK contacts. Primary contact from the provider may be through telephone call, e-mail and SMS text messaging. The message may include the location of the incident, and indication of whether the casualty requires evacuation, and the like. Alternatively, the message may include the health care facility to which the casualty is to be transported, along with contact information for the facility.

ERInfo Server Side Applications

ERInfo may comprise six major server side applications. One part of the system is the participant creating and registering their profile 41 containing the pertinent health information they want to share in the event of an emergency and their image. This component allows for secure capture of the participant's health information for use in the event of an emergency and may include a master image (or images) for the facial recognition engine (either through ERInfo or a via social network based recognition engine) to "match" the presenting image, taken at the time of an emergency event with one or more master images.

A second component of the server side applications provides for the storage and retrieval of the participant's information. In a preferred embodiment, the participant information is stored on through the server side application 41, which includes a registration database that may contain participant demographic data, participant master identification image(s), participant health profile information, and participant billing information. Representative data fields may be seen in reference to FIG. 3.

A third server side application comprises a facial recognition engine 42. The facial recognition engine 42 can either be run on a proprietary server or it may be run with a third party network authentication and user profile retrieval engine 44 to leverage a companion application program interface hosted by a third party social network provider (like Facebook). The role of the facial recognition engine 42 is to perform the facial recognition function on a presenting image received from the provider application 50 and to match, retrieve, and return the relevant participant information 16 from the registration database 41 or via the third party network profile retrieval 44 to the emergency provider.

In addition to forwarding participant information 16 to the provider, the facial recognition engine 42 may also work in conjunction with the ICE/NOK engine 61 to transmit a message to one or more of the participant's mobile device 12, social network messaging functionality, or e-mail address to notify the participant that the system has matched their identity to a casualty and has transmitted their information to a first responder. This notification may prevent mis-identification of a casualty in the event the message recipient is not the identified casualty. Moreover, it may also serve as a check on the unauthorized use of the system by a medical provider or by some other party with access to the provider's device or account.

Figure 6:
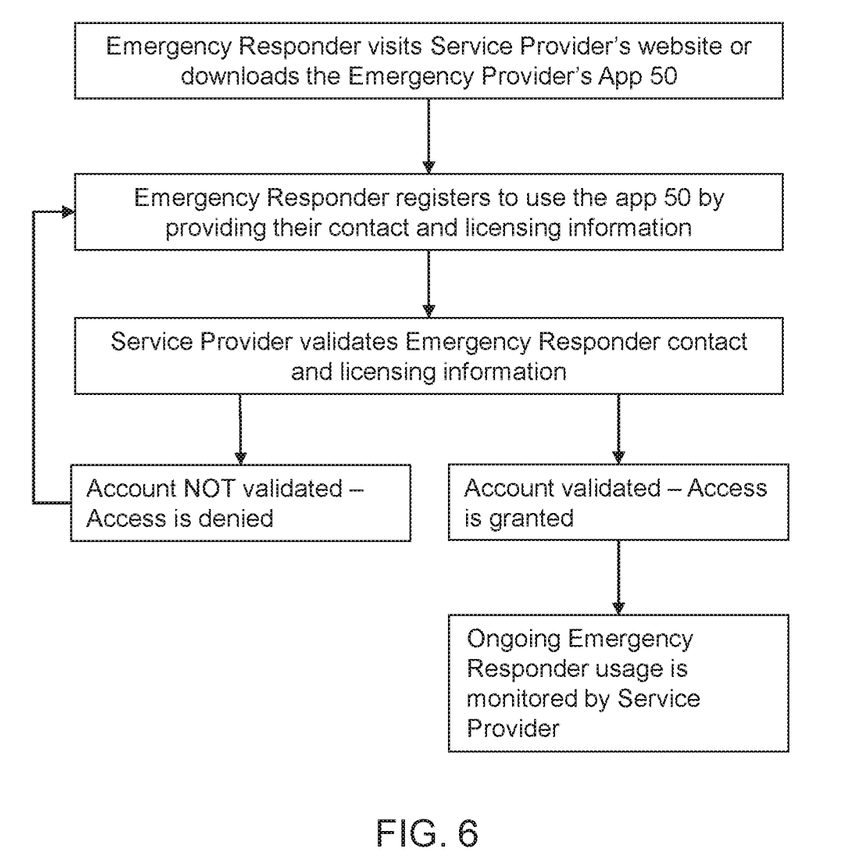
FIG. 6 is a representative flow chart for an Emergency Responder registration & ongoing access verification process.

A fourth server side application may comprise a provider authentication application 43. The provider authentication application 43 manages an emergency provider database to ensure that only authorized users of the system 10 can access the facial recognition application 42 and receive participant identification and health condition data 41. As seen in reference to FIG. 6, Provider authentication application 43 may also include a verification of the provider's credentials with various state, regional, and national registries.

As previously indicated, a fifth server side application may comprise a notification engine 61 configured to automatically, or semi-automatically contact the casualty's ICE/NOK. The notification engine 61 may utilize one or more of an e-mail, SMS, or telephonic communications to provide a notification 62 and pertinent information to the respective ICE/NOK.

A sixth server side application may include a third party integration controller 45. This application manages the interaction with third party web sites that offer consumer registration and billing services from ERInfo on a private label basis.

Collectively these components make up a preferred embodiment of the system. It will be appreciated that all of the components of the system may be extensible. For example, in a limited implementation, participant information could be entered and stored with hidden profile information contained in the participant's social network profile, such as Facebook. Similarly, the facial recognition and information retrieval could leverage the Facebook platform, and the Emergency provider's interface to upload the participant's field image and retrieve the participant's information if a match exists. In this example, Facebook's Application Programming Interface (API) and custom software written using it would create and integrate the components.

In a generalized implementation, the system and method may be developed with custom software and run on proprietary servers to provide the participant registration, facial recognition and data storage and retrieval functionality. Similarly, the emergency provider application could also be implemented utilizing custom applications using the Android SDK to run on Android based phone, the IOS SDK to run on Apple iPhones, and HTML 5 or Java to run in browsers. The computer-based data processing system and method described above is for purposes of example only, and may be implemented in any type of computer system or programming or processing environment, or in a computer program, alone or in conjunction with hardware. The present invention may also be implemented in software stored on a computer-readable medium and executed as a computer program on a general purpose or special purpose computer. For clarity, only those aspects of the system germane to the invention are described, and product details well known in the art are omitted. For the same reason, the computer hardware is not described in further detail. It should thus be understood that the invention is not limited to any specific computer language, program, or computer.

It is further contemplated that the present invention may be run from a server computer system that can be accessed by a plurality of client computer systems interconnected over an intranet network, or that is accessible to clients over the Internet. To the extent the present application discloses a system, the method implemented by that system, as well as software stored on a non-transitory ccomputer readable medium and executed as a computer program to perform the method on a general purpose or special purpose computer, are within the scope of the present invention. Further, to the extent the present application discloses a method, a system of apparatuses configured to implement the method are within the scope of the present invention.

The ERInfo.me system may also provide interfaces or a gateway to a participants Electronic Health Record. The participant registration database can also be transformed to an anonymous database of participant pre-existing healthcare conditions (useful to drug companies, advocacy groups, epidemiologists, and disease specialists).

It should be understood, of course, that the foregoing relates to exemplary embodiments of the invention and that modifications may be made without departing from the spirit and scope of the invention as set forth in the following claims.

What is claimed is:

1. A method of automatically identifying a casualty, comprising:
   receiving a presenting image of the casualty at a server hosted by a casualty identification service, the presenting image captured by a camera of a mobile computing device of a medical first responder in an emergency medical service system, the server in communication with a database containing a master image and an identity profile corresponding to a member of the casualty identification service;
   running a facial recognition engine to compare the presenting image to the master image;
   determining a matching identity of the casualty based on a matching of the presenting image to the master image of the member; and
   when the matching identity is found:
      transmitting the identity profile of the member to at least one of the medical first responder and a medical provider in an emergency medical services system;
   when the matching identity is not found;
      running a social network interface configured to determine the matching identity of the casualty based on the matching of the presenting image to a profile image at least one of a plurality of users in a participating social network utilizing a facial recognition engine of the participating social media network; and
      when the matching identity is found on the participating social network;
         transmitting at least one social network user identity to at least one of the medical first responder and the medical provider.

2. The method of claim 1, wherein the identity profile further comprises:
   one or more health conditions pertaining to the member.

3. The method of claim 2, wherein the identity profile further comprises:
   In Case of Emergency (ICE) contact information pertaining to the member.

4. The method of claim 3, wherein the identity profile further comprises:
   one or more allergy conditions pertaining to the member.

5. The method of claim 3, further comprising:
   verifying the ICE contacts.

6. The method of claim 5, further comprising:
   providing a notification to one or more of the ICE contacts if the member is identified as the casualty.

7. The method of claim 1, further comprising:
   verifying the medical credentials of the first responder.

8. The method of claim 1, further comprising:
   monitoring access to the casualty identification system by the first responder.

9. The method of claim 1, the social network user identity further comprising:
   ICE contact information registered with the participating social media network.

10. The method of claim 9, the social network user identity further comprising:
    one or more health conditions pertaining to the user registered with to the participating social media network.

11. A system for automatically identifying a casualty, comprising:
    a server hosted by a casualty identification service, the server in communication with a database containing a master image and an identity profile corresponding to a member of the casualty identification service;
    a mobile computing device operated by an emergency medical services provider, configured to capture a presenting image of the casualty with a camera operatively connected to the mobile computing device, the mobile computing device configured to transmit the presenting image to the server;
    a facial recognition engine that compares the presenting image to the master image to determine a matching member identity profile of the casualty, when the matching identity is found, the server is configured to transmit the identity profile of the member to the mobile computing device; and
    an application program interface (API) in communication with a participating online social media network, the API configured to determine a matching social media identity of the casualty when the matching identity is not found by the facial recognition engine, the matching social media identity determined based on the matching of the presenting image to a profile image of at least one of a plurality of users in the participating social media network utilizing a facial recognition engine hosted by the participating social media network, and returning one of the matching social media identity of the casualty or a null result to the mobile computing device.

12. The system of claim 11, further comprising:
    an emergency provider database, and
    an authentication application on the mobile computing device wherein a provider authentication through the emergency provider database enables the mobile computing device to receive one of the member identity profile or the user identity corresponding to the casualty.

13. The system of claim 11, further comprising:
    an application program interface (API) in communication with a participating online social media network, configured to link the user's social media profile with to the casualty information service via the participating online social media network.

14. The system of claim 13, wherein the presenting image is compared to an identified image of the member on the social media network.

15. A computer program product stored on a non-transitory computer storage medium comprising machine-readable program code for causing, when executed, a computer to perform the following process steps:
    receive a presenting image of a casualty at a server hosted by a casualty identification service,
    running a facial recognition engine to compare the presenting image to a master image associated with an identity profile of a member of the casualty identification service;
    determining a matching identity of the casualty; when a matching identity is found:
    transmitting the identity profile of the member to a medical provider in an emergency medical services system;
       when the matching identity is not found: running a social network interface configured to determine the matching identity of the casualty based on the matching of the presenting image to a profile image at least one of a plurality of users in a participating social network utilizing a facial recognition engine of the participating social media network; and when the matching identity is found on the participating social network;

transmitting at least one social network user identity to the medical provider.

16. The computer program product of claim 15, wherein the member identity profile further comprises one or more of:

a health condition pertaining to the member;

an In Case of Emergency (ICE) contact information pertaining to the member;

an allergy condition pertaining to the member; and a medicine taken by the member.

17. The computer program product of claim 15, further comprising:

a third party website integration controller, configured to permit an applicant register with the casualty identification service.

18. The computer program product of claim 15, further comprising:

accessing a profile on a participating social media network; and performing the facial recognition on the participating social media network.

19. The computer program product of claim 15, wherein a user profile on the participating social media network further comprises one or more of:

a health condition pertaining to the member;

an In Case of Emergency (ICE) contact information pertaining to the member;

an allergy condition pertaining to the member; and a medicine taken by the member.

* * * * *